United States Patent
Mahajan et al.

(10) Patent No.: US 10,631,744 B2
(45) Date of Patent: Apr. 28, 2020

(54) AF MONITOR AND OFFLINE PROCESSING

(71) Applicant: Cardiac Pacemakers, Inc., St. Paul, MN (US)

(72) Inventors: Deepa Mahajan, Roseville, MN (US); David L. Perschbacher, Coon Rapids, MN (US); Pramodsingh H. Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 155 days.

(21) Appl. No.: 15/486,163

(22) Filed: Apr. 12, 2017

(65) Prior Publication Data

US 2017/0296076 A1 Oct. 19, 2017

Related U.S. Application Data

(60) Provisional application No. 62/322,131, filed on Apr. 13, 2016.

(51) Int. Cl.
*A61B 5/024* (2006.01)
*A61B 5/00* (2006.01)
(Continued)

(52) U.S. Cl.
CPC .......... *A61B 5/02438* (2013.01); *A61B 5/002* (2013.01); *A61B 5/02405* (2013.01);
(Continued)

(58) Field of Classification Search
CPC . A61B 5/02438; A61B 5/02405; A61B 5/002; A61B 5/0456; A61B 5/046; A61N 1/37; A61N 1/36592; A61N 1/3621
See application file for complete search history.

(56) References Cited

U.S. PATENT DOCUMENTS 4,172,459 A 10/1979 Hepp
4,552,154 A 11/1985 Hartlaub
(Continued)

FOREIGN PATENT DOCUMENTS

| WO | WO9965393 A1 | 12/1999 |
| WO | 2009114755 A2 | 9/2009 |
| WO | 2011034468 A1 | 3/2011 |

OTHER PUBLICATIONS

International Search Report and Written Opinion issued in PCT/US2017/012641, dated Apr. 24, 2017, 14 pages.
(Continued)

*Primary Examiner* — Catherine M Voorhees
*Assistant Examiner* — Roland Dinga
(74) *Attorney, Agent, or Firm* — Faegre Drinker Biddle & Reath LLC

(57) ABSTRACT

A system for monitoring a subject for an arrhythmia includes an external monitoring device (EMD) configured to be disposed outside of a subject's body. The EMD includes a first communication component configured to receive, from a medical device, a first physiological parameter signal and an indication of a detected trigger event associated with a first portion of the first physiological parameter signal. The trigger event is indicative of a potential arrhythmia. The EMD also includes an analysis component configured to (1) identify a second portion of the first physiological parameter signal, where the second portion satisfies a discard criterion, (2) discard the second portion, and (3) perform an arrhythmia confirmation evaluation using a third portion of the first physiological parameter signal.

17 Claims, 4 Drawing Sheets

(51) Int. Cl.
  *A61B 5/0456* (2006.01)
  *A61B 5/046* (2006.01)
  *A61N 1/362* (2006.01)
  *A61N 1/365* (2006.01)
  *A61N 1/37* (2006.01)

(52) U.S. Cl.
  CPC ............ *A61B 5/046* (2013.01); *A61B 5/0456* (2013.01); *A61N 1/3621* (2013.01); *A61N 1/36592* (2013.01); *A61N 1/37* (2013.01)

(56) References Cited

U.S. PATENT DOCUMENTS

| | | | |
|---|---|---|---|
| 5,127,404 A | | 7/1992 | Wyborny et al. |
| 5,251,621 A | * | 10/1993 | Collins .............. A61N 1/36042 600/17 |
| 5,800,466 A | | 9/1998 | Routh et al. |
| 5,833,623 A | | 11/1998 | Mann et al. |
| 5,902,250 A | | 5/1999 | Verrier et al. |
| 5,904,708 A | | 5/1999 | Goedeke |
| 6,073,049 A | | 6/2000 | Alt et al. |
| 6,076,015 A | | 6/2000 | Hartley et al. |
| 6,190,324 B1 | | 2/2001 | Kieval et al. |
| 6,490,479 B2 | | 12/2002 | Bock |
| 6,804,558 B2 | | 10/2004 | Haller et al. |
| 6,890,306 B2 | | 5/2005 | Poezevera |
| 6,978,182 B2 | | 12/2005 | Mazar et al. |
| 7,146,206 B2 | | 12/2006 | Glass et al. |
| 7,395,117 B2 | | 7/2008 | Mazar et al. |
| 7,559,903 B2 | | 7/2009 | Moussavi et al. |
| 7,751,876 B2 | | 7/2010 | Healey |
| 7,787,946 B2 | | 8/2010 | Stahmann et al. |
| 7,996,074 B2 | | 8/2011 | Kenknight et al. |
| 8,002,553 B2 | | 8/2011 | Hatlestad et al. |
| 8,049,489 B2 | | 11/2011 | Gauglitz et al. |
| 8,108,048 B2 | | 1/2012 | Masoud |
| 8,126,548 B2 | | 2/2012 | Ding et al. |
| 8,145,590 B2 | | 3/2012 | Brockway et al. |
| 8,209,011 B2 | | 6/2012 | Freeberg |
| 8,396,543 B2 | | 3/2013 | Hoeppner et al. |
| 8,423,142 B2 | | 4/2013 | Freeberg |
| 8,611,000 B2 | | 12/2013 | Komatsu et al. |
| 8,639,318 B2 | | 1/2014 | Hatlestad et al. |
| 8,694,116 B2 | | 4/2014 | Kenknight et al. |
| 8,731,661 B2 | | 5/2014 | White |
| 8,791,815 B2 | | 7/2014 | Mazar et al. |
| 8,849,682 B2 | | 9/2014 | Mahajan et al. |
| 8,915,741 B2 | | 12/2014 | Hatlestad et al. |
| 8,929,981 B2 | | 1/2015 | Perschbacher et al. |
| 8,983,603 B2 | | 3/2015 | Perschbacher et al. |
| 9,014,807 B2 | | 4/2015 | Bocek et al. |
| 9,020,602 B2 | | 4/2015 | Aghassian |
| 9,037,240 B2 | | 5/2015 | Gunderson |
| 9,610,025 B2 | | 4/2017 | Zhang |
| 2001/0051787 A1 | | 12/2001 | Haller et al. |
| 2002/0072783 A1 | | 6/2002 | Goedeke et al. |
| 2003/0028080 A1 | | 2/2003 | Lebel et al. |
| 2005/0042589 A1 | | 2/2005 | Hatlestad et al. |
| 2005/0251227 A1 | | 11/2005 | Khoo et al. |
| 2005/0288599 A1 | | 12/2005 | MacAdam et al. |
| 2006/0241708 A1 | | 10/2006 | Boute |
| 2007/0255330 A1 | | 11/2007 | Lee et al. |
| 2007/0286469 A1 | | 12/2007 | Yamagata et al. |
| 2008/0183245 A1 | | 7/2008 | van Oort et al. |
| 2009/0058635 A1 | | 3/2009 | LaLonde et al. |
| 2009/0063187 A1 | | 3/2009 | Johnson et al. |
| 2009/0088821 A1 | | 4/2009 | Abrahamson |
| 2010/0057167 A1 | | 3/2010 | Evers et al. |
| 2010/0152815 A1 | | 6/2010 | Vandanacker |
| 2010/0185251 A1 | | 7/2010 | Propato |
| 2010/0241182 A1 | * | 9/2010 | Whitman ............. A61B 5/0215 607/5 |
| 2010/0280841 A1 | | 11/2010 | Dong et al. |
| 2011/0046698 A1 | * | 2/2011 | Kivi .................... H04W 76/19 607/60 |
| 2011/0270109 A1 | | 11/2011 | Zhang et al. |
| 2012/0029373 A1 | | 2/2012 | Stadler et al. |
| 2012/0078131 A1 | | 3/2012 | Zong |
| 2012/0154152 A1 | | 6/2012 | Rantala et al. |
| 2012/0165887 A1 | | 6/2012 | Lee et al. |
| 2012/0188096 A1 | | 7/2012 | Corndorf et al. |
| 2012/0232416 A1 | | 9/2012 | Gilham et al. |
| 2012/0253207 A1 | | 10/2012 | Sarkar et al. |
| 2012/0283544 A1 | | 11/2012 | Kraetschmer et al. |
| 2012/0296228 A1 | | 11/2012 | Zhang et al. |
| 2013/0237773 A1 | | 9/2013 | An et al. |
| 2013/0274624 A1 | | 10/2013 | Mahajan et al. |
| 2014/0277243 A1 | | 9/2014 | Maskara et al. |
| 2015/0216433 A1 | | 8/2015 | Thakur et al. |
| 2015/0282738 A1 | | 10/2015 | Thakur et al. |
| 2015/0342487 A1 | | 12/2015 | Thakur et al. |
| 2016/0045125 A1 | | 2/2016 | Krueger et al. |
| 2017/0196457 A1 | | 7/2017 | Thakur et al. |
| 2017/0199970 A1 | | 7/2017 | Stahmann et al. |
| 2017/0251940 A1 | | 9/2017 | Perschbacher et al. |
| 2017/0290528 A1 | | 10/2017 | Ternes et al. |

OTHER PUBLICATIONS

International Search Report and Written Opinion issued in PCT/US2017/012649, dated Mar. 29, 2017, 18 pages.
International Search Report and Written Opinion issued in PCT/US2017/012651, dated Mar. 24, 2017, 12 pages.
International Search Report and Written Opinion issued in PCT/US2017/020831, dated Jun. 16, 2017, 11 pages.
Passman, Rod S., et al, "Development and Validation of a Dual Sensing Scheme to Improve Accuracy of Bradycardia and Pause Detection in an Insertable Cardiac Monitor." Heart Rhythm, 14:1016-1023, 2017.
Sarkar, Shantanu, et al. "A Dual Sensing Scheme to Reduce Inappropriate Detection of Bradycardia and Pauses in an Insertable Cardiac Monitor." 2016 Heart Rhythm, 15 pages.
International Preliminary Report on Patentability issued in PCT/US2017/012641, dated Jul. 19, 2018, 9 pages.
International Preliminary Report on Patentability issued in PCT/US2017/012649, dated Jul. 19, 2018, 10 pages.
International Preliminary Report on Patentability issued in PCT/US2017/012651, dated Jul. 19, 2018, 8 pages.
International Preliminary Report on Patentability issued in PCT/US2017/020831, dated Sep. 13, 2018, 7 pages.

* cited by examiner

AF MONITOR AND OFFLINE PROCESSING

CROSS-REFERENCE TO RELATED APPLICATION

This application claims priority to Provisional Application No. 62/322,131, filed Apr. 13, 2016, which is herein incorporated by reference in its entirety.

TECHNICAL FIELD

The present disclosure relates to monitoring subjects for arrhythmia. More specifically, embodiments of the disclosure relate to systems and method for atrial fibrillation detection and confirmation.

BACKGROUND

If patient has a lead in the atrium, it can be fairly straightforward to monitor them accurately for AF. However, for devices without a lead in the atrium, R-R variability typically is used to detect AF. Limitations of that technique include, for example, false alerts and a risk of missing shorter AF episodes.

SUMMARY

In an Example 1, a system, comprising: an external monitoring device (EMD) configured to be disposed outside of a subject's body, the EMD comprising: a first communication component configured to receive, from a medical device, a first physiological parameter signal and an indication of a detected trigger event associated with a first portion of the first physiological parameter signal, wherein the trigger event is indicative of a potential arrhythmia; and an analysis component configured to (1) identify a second portion of the first physiological parameter signal, wherein the second portion satisfies a discard criterion, (2) discard the second portion, and (3) perform an arrhythmia confirmation evaluation using a third portion of the first physiological parameter signal.

In an Example 2, the system of Example 1, wherein the trigger event comprises a potential atrial fibrillation episode.

In an Example 3, the system of Example 2, further comprising the medical device, the medical device comprising: a sensing component configured to obtain the first physiological parameter signal; a trigger component configured to detect the trigger event by: calculating a first R-R variability associated with the first portion of the first physiological parameter signal; and determining that the first R-R variability exceeds a variability threshold; and a second communication component configured to transmit the physiological parameter signal to the first communication component.

In an Example 4, the system of Example 3, wherein the trigger component is configured to cause, in response to detecting the trigger event, the second communication component to transmit the first physiological parameter signal to the first communication component.

In an Example 5, the system of either of Examples 3 or 4, wherein the analysis component is configured to identify the second portion of the first physiological parameter signal by: identifying a set of beat pairs within a specified neighborhood of the variability threshold; and detecting at least one of a P-wave and an S4 heart sound corresponding to each of a subset of the set of beat pairs, wherein the subset of beat pairs comprises the second portion of the first physiological parameter signal.

In an Example 6, the system of Example 5, wherein the sensing component is further configured to obtain a second physiological parameter signal, the second physiological parameter signal comprising a heart sounds signal.

In an Example 7, the system of any of Examples 3-6, wherein the analysis component is configured to perform the arrhythmia confirmation algorithm by: calculating a second R-R variability associated with the third portion of the first physiological parameter signal; and determining that the second R-R variability exceeds the variability threshold.

In an Example 8, the system of any of Examples 1-7, wherein the analysis component is further configured to: divide the first portion of the first physiological signal into a plurality of sections; identify a first portion of each of the plurality of sections, wherein the first portion of each of the plurality of sections satisfies the discard criterion; discard the first portion of each of the plurality of sections; and perform an arrhythmia confirmation evaluation using a second portion of each of the plurality of sections.

In an Example 9, the system of any of Examples 3-8, wherein the medical device comprises an implantable medical device.

In an Example 10, a method of monitoring a subject for arrhythmia, the method comprising: receiving, from a medical device, a first physiological parameter signal and an indication of a detected trigger event associated with a first portion of the first physiological parameter signal, wherein the trigger event is indicative of a potential arrhythmia; determining that a second portion of the first physiological parameter signal satisfies a discard criterion; discarding the second portion; and performing an arrhythmia confirmation evaluation using a third portion of the first physiological parameter signal.

In an Example 11, the method of Example 10, wherein determining that a second portion of the first physiological parameter signal satisfies a discard criterion comprises: identifying a set of beat pairs within a specified neighborhood of a variability threshold; and detecting at least one of a P-wave and an S4 heart sound corresponding to each of a subset of the set of beat pairs, wherein the subset of beat pairs comprises the second portion of the first physiological parameter signal.

In an Example 12, the method of Example 11, further comprising receiving a second physiological signal, the second physiological signal comprising a heart sounds signal.

In an Example 13, the method of either of Examples 11 or 12, wherein the trigger event is detected based on a first R-R variability associated with a first portion of the physiological signal, and wherein performing the arrhythmia confirmation algorithm comprises: calculating a second R-R variability associated with the third portion of the first physiological parameter signal; and determining that the second R-R variability exceeds the variability threshold.

In an Example 14, the method of any of Examples 10-13, further comprising: dividing the first portion of the first physiological signal into a plurality of sections; determining that a first portion of each of the plurality of sections satisfies the discard criterion; discarding the first portion of each of the plurality of sections; and performing an arrhythmia confirmation evaluation using a second portion of each of the plurality of sections.

In an Example 15, the method of either of Examples 13 or 14, further comprising detecting the trigger event by:

calculating the first R-R variability associated with the first portion of the first physiological parameter signal; and determining that the first R-R variability exceeds the variability threshold.

In an Example 16, a system, comprising: a medical device operatively coupled to a subject's body, the medical device comprising: a sensing component configured to obtain a first physiological parameter signal; a trigger component configured to detect, based on a first portion of the first physiological parameter signal, a trigger event indicative of a potential arrhythmia; a first communication component configured to transmit the first physiological parameter signal; and an external monitoring device (EMD) configured to be disposed outside of the subject's body, the EMD comprising: a second communication component configured to receive, from the first communication component, the first physiological parameter signal; and an analysis component configured to (1) identify a second portion of the first physiological parameter signal, wherein the second portion satisfies a discard criterion, (2) discard the second portion, and (3) perform an arrhythmia confirmation evaluation using a third portion of the first physiological parameter signal.

In an Example 17, the system of Example 16, wherein the trigger event comprises a potential atrial fibrillation episode.

In an Example 18, the system of Example 17, wherein the trigger component is configured to detect the trigger event by: calculating a first R-R variability associated with the first portion of the first physiological parameter signal; and determining that the first R-R variability exceeds a variability threshold.

In an Example 19, the system of Example 18, wherein the trigger component is configured to cause, in response to detecting the trigger event, the first communication component to transmit the first physiological parameter signal to the second communication component.

In an Example 20, the system of Example 18, wherein the analysis component is configured to identify the second portion of the first physiological parameter signal by: identifying a set of beat pairs within a specified neighborhood of the variability threshold; and detecting at least one of a P-wave and an S4 heart sound corresponding to each of a subset of the set of beat pairs, wherein the subset of beat pairs comprises the second portion of the first physiological parameter signal.

In an Example 21, the system of Example 20, wherein the sensing component is further configured to obtain a second physiological parameter signal, the second physiological parameter signal comprising a heart sounds signal.

In an Example 22, the system of Example 20, wherein the analysis component is configured to perform the arrhythmia confirmation algorithm by: calculating a second R-R variability associated with the third portion of the first physiological parameter signal; and determining that the second R-R variability exceeds the variability threshold.

In an Example 23, the system of Example 16, wherein the analysis component is further configured to: divide the first portion of the first physiological signal into a plurality of sections; identify a first portion of each of the plurality of sections, wherein the first portion of each of the plurality of sections satisfies the discard criterion; discard the first portion of each of the plurality of sections; and perform an arrhythmia confirmation evaluation using a second portion of each of the plurality of sections.

In an Example 24, the system of Example 16, wherein the medical device comprises an implantable medical device.

In an Example 25, a method of monitoring a subject for arrhythmia, the method comprising: receiving, from a medical device, a first physiological parameter signal and an indication of a detected trigger event associated with a first portion of the first physiological parameter signal, wherein the trigger event is indicative of a potential arrhythmia; determining that a second portion of the first physiological parameter signal satisfies a discard criterion; discarding the second portion; and performing an arrhythmia confirmation evaluation using a third portion of the first physiological parameter signal.

In an Example 26, the method of Example 25, wherein determining that a second portion of the first physiological parameter signal satisfies a discard criterion comprises: identifying a set of beat pairs within a specified neighborhood of a variability threshold; and detecting at least one of a P-wave and an S4 heart sound corresponding to each of a subset of the set of beat pairs, wherein the subset of beat pairs comprises the second portion of the first physiological parameter signal.

In an Example 27, the method of Example 26, further comprising receiving a second physiological signal, the second physiological signal comprising a heart sounds signal.

In an Example 28, the method of Example 26, wherein the trigger event is detected based on a first R-R variability associated with a first portion of the physiological signal, and wherein performing the arrhythmia confirmation algorithm comprises: calculating a second R-R variability associated with the third portion of the first physiological parameter signal; and determining that the second R-R variability exceeds the variability threshold.

In an Example 29, the method of Example 28, further comprising detecting the trigger event by: calculating the first R-R variability associated with the first portion of the first physiological parameter signal; and determining that the first R-R variability exceeds the variability threshold.

In an Example 30, the method of Example 29, wherein performing the arrhythmia confirmation evaluation using the third portion of the first physiological parameter signal comprises: detecting a plurality of R waves using a morphology analysis; and calculating the second R-R variability based on the plurality of R waves.

In an Example 31, the method of Example 25, wherein the medical device comprises an implantable medical device.

In an Example 32, the method of Example 26, further comprising: dividing the first portion of the first physiological signal into a plurality of sections; determining that a first portion of each of the plurality of sections satisfies the discard criterion; discarding the first portion of each of the plurality of sections; and performing an arrhythmia confirmation evaluation using a second portion of each of the plurality of sections.

In an Example 33, a method of monitoring a subject for arrhythmia, the method comprising: receiving a first physiological parameter signal and an indication of a detected trigger event associated with a first portion of the first physiological parameter signal, wherein the trigger event is indicative of a potential arrhythmia; dividing the first portion of the first physiological parameter signal into a plurality of sections; determining that a first portion of each of the plurality of sections satisfies a discard criterion; discarding the first portion of each of the plurality of sections; and performing an arrhythmia confirmation evaluation using a second portion of each of the plurality of sections.

In an Example 34, the method of Example 33, wherein determining that a first portion of a first section of the plurality of sections of the first portion of the first physiological parameter signal satisfies a discard criterion comprises: identifying a set of beat pairs within a specified neighborhood of a variability threshold; and detecting at least one of a P-wave and an S4 heart sound corresponding to each of a subset of the set of beat pairs.

In an Example 35, the method of Example 34, wherein performing the arrhythmia confirmation evaluation using a second portion of the first section comprises: calculating an R-R variability associated with the second portion of the first section; and determining that the R-R variability exceeds the variability threshold.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
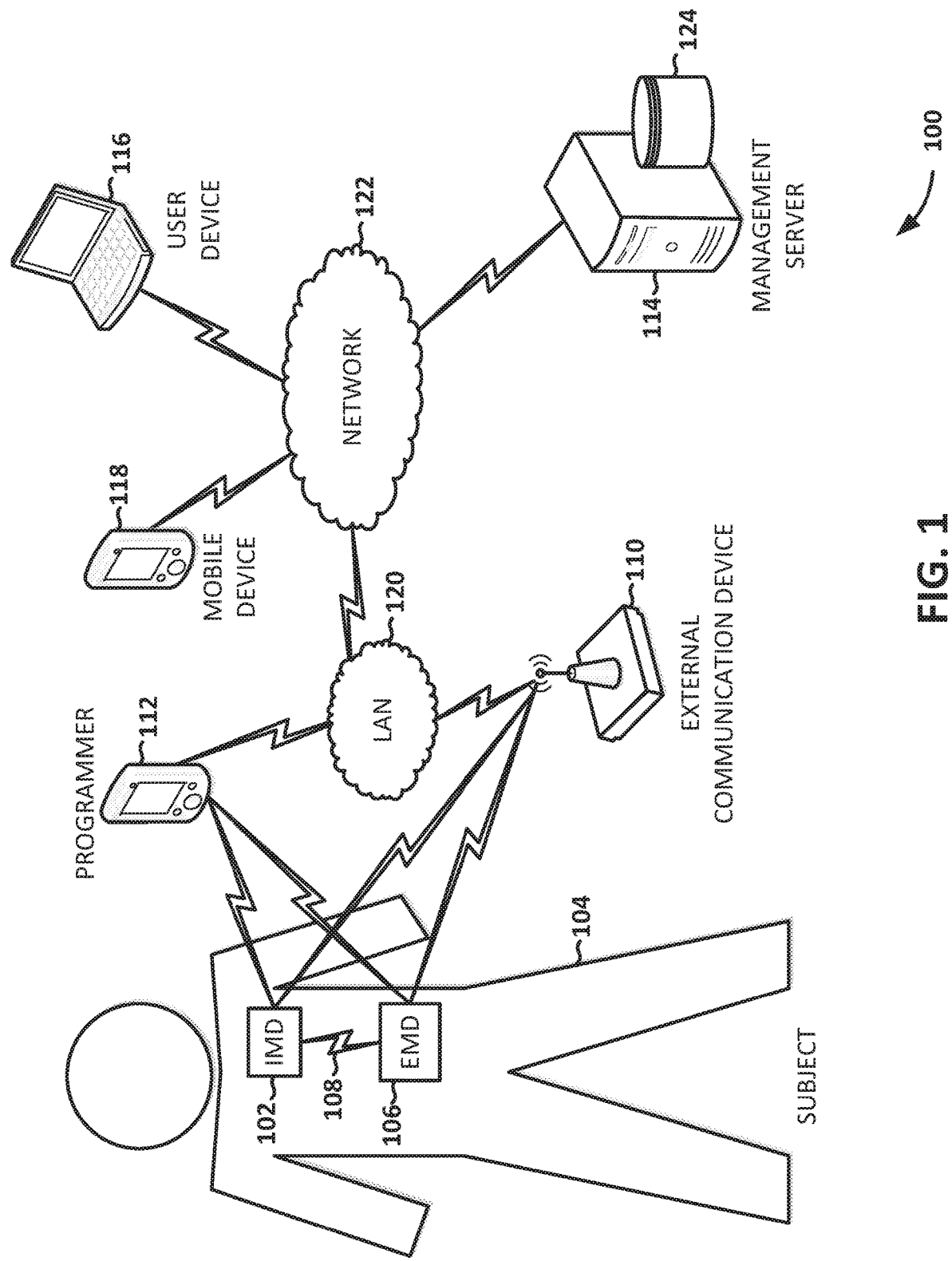
FIG. 1 shows an illustrative medical system, in accordance with embodiments of the present disclosure.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps. Additionally, a "set" or "group" of items (e.g., inputs, algorithms, data values, etc.) may include one or more items, and, similarly, a subset or subgroup of items may include one or more items.

DETAILED DESCRIPTION

Embodiments include systems, devices, and/or processes that may be utilized for monitoring AF patients and/or patients with elevated risk factors of stroke due to AF. Additionally, it embodiments may be used to monitor patients on anticoagulant therapy, e.g., to evaluate its efficacy. Monitoring these patients may help them get therapy early enough to more likely prevent stroke and thereby save on hospitalization costs.

Embodiments of the systems described above may facilitate performing offline analysis for AF detection (e.g., by performing analysis in another device such as, for example, an external monitoring device (EMD), a server, and/or the like). This may facilitate improved accuracy, as well as device longevity.

For example, in an implementation, an AF algorithm in a medical device (e.g., an implantable medical device (IMD) or a wearable medical device) may be tuned to be very sensitive. When an AF trigger event is detected (e.g., by a trigger component implemented by the medical device), the medical device may be configured to transmit EGM and other sensor data to an EMD for analysis. The "offline" AF algorithm may be tuned for accuracy. In this manner, the more sensitive algorithm executing in the medical device may be able to more easily identify trigger events, but each trigger event can be confirmed or dismissed based on a more accurate algorithm executed externally, thereby increasing the possibility of detecting AF while decreasing the instances of false alarms.

According to embodiments, the medical device and offline algorithms may be the same algorithms with different thresholds, or different algorithms. For example, the algorithm in the medical device may be based on onset of the arrhythmia and may include a detector that simply detects sudden heart rate change. A sudden heart rate change may be detected by running a step detection on a trend of successive R-R intervals. For example, a set of N successive R-R intervals that deviate by a certain threshold (e.g., mean plus standard deviation) from prior M beats (e.g., prior to the recent N beats) can trigger a step detection. The offline algorithm can be more computationally expensive since it can be implemented on an external computing device (e.g., a programmer, an external monitoring device, a computer, a server, etc.) instead of a medical device. In embodiments, the offline analysis may be based on EGMs, along with information from other implanted and/or external sensors. In embodiments, the offline algorithm may be based on R-R variability, heat rate density index, heart sounds, and/or the like.

According to embodiments, a trigger component (which may include operational components of a medical device, an EMD, and/or the like) may be used to run a "real-time" trigger detection process that is used to trigger a "non-real-time" analysis (the "offline" analysis). The trigger event for "offline analysis" may include, for example, a simple real-time onset detector, an input through a patient app (e.g., where the patient clicks a button on his/her application indicating he/she is not feeling well/feeling queasy, lightheaded, etc.), and/or the like. For example, in embodiments, the trigger detection process may include a simple onset detector (e.g., implementing a step detection algorithm as described above), while the offline analysis includes RR variability and heart sounds-based algorithms. In another implementation, the trigger detection process may include a simple onset detector and RR variability analysis, while the offline analysis includes heart sounds-based algorithms. Upon detecting a trigger event, the medical device may implement a study prescription that causes the medical device to dump the entire episode data for offline analysis, or certain regions of interest. Study prescriptions refer to sets of instructions, conditions, protocols, and/or the like, that specify one or more of an information gathering scheme and a communication scheme, and may be configured, for example, to obtain information at a resolution sufficient for performing a certain analysis (e.g., associated with a diagnostic model), while managing the resulting impact to device longevity and/or performance. For example, in the R-R variability framework, the medical device might just transmit "borderline beats" e.g., beats that are close to the thresholds, together with relevant sensor data (heart sounds, activity, etc.) for closer scrutiny of those beats and re-classification.

In embodiments, data is obtained from a medical device by triggering a limited-time system behavior change. Embodiments include utilizing study prescriptions that specify one or more criteria, procedures, parameters, and/or other aspects of obtaining the data. For example, study prescriptions may facilitate enabling sensor components, obtaining data, analyzing data, batching data obtained by a medical device, communicating the batched data to an external device, reconstructing the batched data at the external device, and/or the like. Study prescriptions may also include instructions for configuring one or more sensors, modifying one or more filters, modifying one or more sensor inputs (e.g. by changing a vector measured by a minute volume (MV) impedance component from focusing on changes in a lung to focusing on stroke volume of the heart), modifying one or more sensing parameters (e.g., sampling rate, sample storage rate, sensing thresholds, sensing durations), and/or the like. In some embodiments, the first trigger may automatically trigger collection and transmission of data to the EMD.

In this manner, for example, a particular sensor may be generally disabled (e.g., because it consumes relatively large amounts of power, is not necessary for a day-to-day or beat-to-beat operation), but may be able to be enabled in response to execution of instructions of a study prescription and/or in response to the first trigger. For example, in embodiments, the filters of an accelerometer may be modified, according to a study prescription, to analyze data in different frequency ranges. In an implementation, for example, an IMD may be configured to generally use an accelerometer to drive rate and sample sensed measurements in a first frequency range, e.g., to facilitate rate-responsive pacing.

In embodiments, a clinician may determine a need or desire for obtaining data (information) from an IMD and may discuss this need for the data with the patient, after which the clinician may "prescribe" the data gathering study. The patient's implanted device may be set up to transmit data for prescribed period of time (e.g., automatically, via a wearable external monitoring device). The data may be, for example, transmitted in a continuous RF communication, batched, and/or the like. In embodiments, batching data may be dependent on a multitude of factors, e.g., the studies conducted, what channels are recording by default, whether any channels kick in after the first channel records something of interest for a study, and/or the like.

Embodiments may include any number of different considerations that may facilitate maximizing (or at least enhancing) data gathering while minimizing (or at least reducing) resulting impacts on the longevity of one or more components of the IMD. Such considerations may include, for example, storage capacity, power source depletion; and/or the like. Any number of various techniques may be implemented to facilitate these and/or other objectives. For example, rolling buffers may be implemented for managing the stored information. In embodiments, data may be overlapped to account for missed transmissions, such that when external devices piece the data back together (e.g., based on time stamps), the data may complete, and repeated data can be discarded. Data may also be synchronized with data from other sensors so that one parameter may be analyzed in the context of one or more other parameters. Any number of techniques for synchronizing data may be utilized including, for example, using sync signals as described in U.S. Application No. 62/276,686, titled "SYNCING MULTIPLE SOURCES OF PHYSIOLOGICAL DATA," filed concurrently herewith, the disclosure of which is hereby incorporated by reference herein in its entirety. In embodiments, the IMD may be configured to sense information at a lower resolution unless a trigger event (described in more detail below) is detected, at which time data may be gathered at a higher resolution. In embodiments, an external device may be passive and/or may actively request data from the IMD.

In embodiments, the number of times a study prescription can be enabled may be limited by the prescription, the IMD, the external device, and/or the like. In embodiments, a study prescription may also cause an IMD to provide information associated with the cumulative impact to the longevity of the IMD from implementing the study prescription, and may prompt a server or other device to obtain confirmation from a user before authorizing implementation of another study prescription, or another implementation of the same study prescription. Similarly, the IMD may perform a study prescription in stages, providing longevity impact information after the completion of each stage (with the system, perhaps, requiring a user confirmation to continue with the study prescription after each stage).

Additionally, to enhance efficiency, a study prescription may cause an IMD to turn off one or more channels when the IMD is gathering data. In embodiments, the study prescription may be configured to cause the IMD to first obtain the information that has the lowest longevity impact cost initially and then to dynamically determine how much additional information is needed, as captured information is analyzed. Embodiments may also facilitate dynamically switching frequencies at which communications are conducted, dynamically adjusting data sampling rates, data batching frequencies, and/or the like. Additionally, embodiments may facilitate remotely programming IMDs (e.g., to be remotely turned off, to remotely enable study prescriptions, to remotely adjust therapy, and/or the like).

FIG. 1 shows an illustrative medical system 100, in accordance with embodiments of the disclosure. As shown in FIG. 1, the medical system 100 includes an IMD 102 configured to be implanted within the body of a subject 104, and an external monitoring device (EMD) 106, which is communicatively coupled to the IMD 102 via a communication link 108. In the illustrated embodiments, the medical system 100 is operatively coupled to the subject 104, and the IMD 102 is configured to communicate with the EMD 106 over the communication link 108. The subject 104 may be a human, a dog, a pig, and/or any other animal having physiological parameters that can be recorded. For example, in embodiments, the subject 104 may be a human patient.

In embodiments, the communication link 108 may be, or include, a wireless communication link such as, for example, a short-range radio link, such as Bluetooth, IEEE 802.11, a proprietary wireless protocol, and/or the like. In embodiments, for example, the communication link 108 may utilize Bluetooth Low Energy radio (Bluetooth 4.1), or a similar protocol, and may utilize an operating frequency in the range of 2.40 to 2.48 GHz. The term "communication link" may refer to an ability to communicate some type of information in at least one direction between at least two devices, and should not be understood to be limited to a direct, persistent, or otherwise limited communication channel. That is, according to embodiments, the communication link 108 may be a persistent communication link, an intermittent communication link, an ad-hoc communication link, and/or the like. The communication link 108 may refer to direct communications between the IMD 102 and the EMD 106, and/or indirect communications that travel between the IMD 102 and the EMD 106 via at least one other device (e.g., a repeater, router, hub, and/or the like). The communication link 108 may facilitate uni-directional and/or bi-directional communication between the IMD 102 and the EMD 106. Data and/or control signals may be transmitted between the IMD 102 and the EMD 106 to coordinate the functions of the IMD 102 and/or the EMD 106. In embodiments, patient data may be downloaded from one or more of the IMD 102 and the EMD 106 periodically or on command. The physician and/or the patient may communicate with the IMD 102 and the EMD 106, for example, to acquire patient data or to initiate, terminate and/or modify recording and/or therapy.

In embodiments, the IMD 102 and/or the EMD 106 may provide one or more of the following functions with respect to a patient: sensing, data analysis, and therapy. For example, in embodiments, the IMD 102 and/or the EMD 106 may be used to measure any number of a variety of physiological, device, subjective, and/or environmental parameter signals associated with the subject 104, using electrical, mechanical, and/or chemical means. The IMD 102 and/or the EMD 106 may be configured to automatically gather data, gather data upon request (e.g., input provided by the subject, a clinician, another device, and/or the like), and/or any number of various combinations and/or modifications thereof. The IMD 102 and/or EMD 106 may be configured to store data related to the physiological, device, environmental, and/or subjective parameter signals and/or transmit the data to any number of other devices in the system 100. In embodiments, the IMD 102 and/or the EMD 106 may be configured to analyze data and/or act upon the analyzed data. For example, the IMD 102 and/or EMD 106 may be configured to modify therapy, perform additional monitoring, and/or provide alarm indications based on the analysis of the data.

According to embodiments, the IMD 102 may include any type of IMD, any number of different components of an implantable system, and/or the like. For example, the IMD 102 may include a control device, a monitoring device, a pacemaker, an implantable cardioverter defibrillator (ICD), a cardiac resynchronization therapy (CRT) device and/or the like, and may be an implantable medical device known in the art or later developed, for providing therapy and/or diagnostic data about the subject 104 and/or the IMD 102. In various embodiments, the IMD 102 may include both defibrillation and pacing/CRT capabilities (e.g., a CRT-D device).

In embodiments, the IMD 102 may be implanted subcutaneously within an implantation location or pocket in the patient's chest or abdomen and may be configured to monitor (e.g., sense and/or record) physiological parameters associated with the patient's heart. In embodiments, the IMD 102 may be an implantable cardiac monitor (ICM) (e.g., an implantable diagnostic monitor (IDM), an implantable loop recorder (ILR)) configured to record physiological parameters such as, for example, one or more cardiac electrical signals, heart sounds, heart rate, blood pressure measurements, oxygen saturations, and/or the like.

In embodiments, the IMD 102 may be configured to monitor physiological parameters that may include one or more signals indicative of a patient's physical activity level and/or metabolic level, such as an acceleration signal. In embodiments, the IMD 102 may be configured to sense intrathoracic impedance, from which various respiratory parameters may be derived, including, for example, respiratory tidal volume and minute ventilation. Sensors and associated circuitry may be incorporated in connection with the IMD 102 for detecting one or more body movement or body posture and/or position related signals. For example, accelerometers and/or GPS devices may be employed to detect patient activity, patient location, body orientation, and/or torso position. The IMD 102 may be configured to sense and/or record at regular intervals, continuously, and/or in response to a detected event. For example, in embodiments, the IMD 102 may be configured to detect a trigger event (described in more detail below) and communicate a notification of the trigger event to the EMD 106, which may perform one or more actions to enable a study prescription that may be implemented by the IMD 102 to acquire higher resolution data to confirm the trigger event, classify the trigger event, diagnose a related condition, and/or the like.

In various embodiments, the EMD 106 may be a device that is configured to be portable with the subject 104, e.g., by being integrated into a vest, belt, harness, sticker; placed into a pocket, a purse, or a backpack; carried in the subject's hand; and/or the like, or otherwise operatively (and/or physically) coupled to the subject 104. The EMD 106 may be configured to monitor (e.g., sense and/or record) physiological parameters associated with the subject 104 and/or provide therapy to the subject 104. For example, the EMD 106 may be, or include, a wearable cardiac defibrillator (WCD) such as a vest that includes one or more defibrillation electrodes. In embodiments, the EMD 106 may include any number of different therapy components such as, for example, a defibrillation component, a drug delivery component, a neurostimulation component, a neuromodulation component, a temperature regulation component, and/or the like. In embodiments, the EMD 106 may include limited functionality, e.g., defibrillation shock delivery and communication capabilities, with arrhythmia detection, classification and/or therapy command/control being performed by a separate device such as, for example, the IMD 102.

In embodiments, the EMD 106 may include sensing components such as, for example, one or more surface electrodes configured to obtain an electrocardiogram (ECG), one or more accelerometers configured to detect motion associated with the patient 104, one or more respiratory sensors configured to obtain respiration information, one or more environmental sensors configured to obtain information about the external environment (e.g., temperature, air quality, humidity, carbon monoxide level, oxygen level, barometric pressure, light intensity, sound, and/or the like) surrounding the patient 104, and/or the like. In embodiments, the EMD 106 may be configured to measure parameters relating to the human body, such as temperature (e.g., a thermometer), blood pressure (e.g., a sphygmomanometer), blood characteristics (e.g., glucose levels), body weight, physical strength, mental acuity, diet, heart characteristics, relative geographic position (e.g., a Global Positioning System (GPS)), and/or the like.

According to embodiments, the EMD 106 may be configured to measure subjective and/or perceptive data from the subject 104. Subjective data is information related to a patient's feelings, perceptions, and/or opinions, as opposed, for example, to objective physiological data. For example, EMD 106 may be configured to measure subject responses to inquiries such as "How do you feel?" and "How is your pain?" The EMD 106 may be configured to prompt the subject 104 and record subjective data from the subject 104 using visual and/or audible cues. In embodiments, the subject 104 can press coded response buttons or type an appropriate response on a keypad. In embodiments, subjective data may be collected by allowing the subject 104 to speak into a microphone and using speech recognition software to process the subjective data.

In embodiments, the EMD 106 may include a prescription enabler that may be configured to automatically enable a study prescription when the EMD 106 is within communicating range of the IMD 102. In embodiments, enablement of the study prescription may require a password or other input, which may be received by the EMD 106. In other embodiments, the EMD 106 may include a button, switch, or other actuable mechanism that a patient or clinician may actuate to enable the study prescription. In other embodiments, the study prescription may be enabled at an earlier time (e.g., in the clinician's office, using a wand), but implemented later, in response to an input from the subject indicating, for example, that the subject is going to bed, having a certain feeling, and/or the like. In embodiments, the study prescription may be enabled within the IMD 102 earlier (e.g., in the clinician's office), and implemented only when the subject comes into proximity of the EDM 106 (or enabled within the IMD 102 and/or EMD 106 and implemented when the subject comes into proximity of another external device such as, for example, an external communication device 110).

As shown in FIG. 1, the system 100 includes the external communication device 110 and a programmer 112. In embodiments, the external communication device 110 and/or the programmer 112 may be, be similar to, include, or be included in, the EMD 106, while in other embodiments, the external communication device 110 and/or the programmer 112 may be separate devices from the EMD 106. In embodiments, the external communication device 110 and/or the programmer 112 may be provided to the subject 104 and are often located within the subject's home.

According to embodiments, the external communication device 110 and/or the programmer 112 may be configured to send data to, and receive data from, a device, such as the IMD 102, the EMD 106, the other of the external communication device 110 and the programmer 112, and/or any number of other devices depicted or not depicted in FIG. 1. Such communications may be facilitated via communication links 108B-108I, any number of which may be, be identical to, be similar to, include, be coupled with, or be included within, the communication link 108A. The external communication device 110 and/or programmer 112 may operate as an interrogator of the IMD 102 and/or the EMD 106. In embodiments, the external communication device 110 and/or programmer 112 may perform one or more of the following functions: (1) data storage; (2) data analysis; (3) data forwarding; (4) patient interaction; (5) patient feedback; and (6) data communications. For example, the external communication device 110 and/or programmer 112 may facilitate communications between the devices 102 and 106 and a management server 114, a user device 116, a mobile device 118, and/or the like. The external communication device 110 and/or programmer 112 may, periodically or in real-time, interrogate and download into memory clinically relevant patient data. This data may include, for example, P and R-wave measurements, pacing, shocking events, lead impedances, pacing thresholds, battery voltage, capacitor charge times, ATR episodes with electrograms, tachycardia episodes with electrograms, histogram information, and/or any other clinical information necessary to ensure patient health and proper device function.

In embodiments, the external communication device 110 and/or programmer 112 may communicate with a network 120 that may be, for example, a local area network (LAN) in the subject's home or other location. The external communication device 110 and/or programmer 112 may be configured to systematically obtain information from the devices 102 and/or 106 while the patient is sleeping, for example. The obtained data may be transmitted through the network 120 and/or a network 122 to the management server 114. In addition, in embodiments the external communication device 110 and/or programmer 112 functions in a hybrid form, utilizing wireless communication when available and defaulting to a local wireless portal or a wired connection when the wireless communication becomes unavailable. In embodiments, the network 120 and the network 122 may be integrated within one another, may be the same network, and/or the like.

In embodiments, the external communication device 110 and/or programmer 112 may be in the form of a small device that is placed in an inconspicuous place within the subject's residence and may use radio frequency (RF) to communicate with the IMD 102 and/or EMD 106. The external communication device 110 and/or programmer 112 may be implemented as part of a commonly-used appliance in the subject's residence. For example, the external communication device 110 and/or programmer 112 may be integrated with an alarm clock that is positioned near the subject's bed. In another embodiment, the external communication device 110 and/or programmer 112 may be implemented as part of the subject's personal computer system. In another embodiment, the external communication device 110 and/or programmer 112 may include a hand-held device such as a PDA, cellular telephone, or other similar. The hand-held device may upload data to the management server 114 wirelessly. Additionally, or alternatively, the hand-held device may periodically be placed in a cradle or other similar device that is configured to transmit the data to the management server 114. In embodiments, the external communication device 110 and/or programmer 112 may perform analysis on data and provide immediate feedback, as well as perform a variety of self-diagnostic tests to verify that it is functioning properly and that communication with one or more other devices has not be compromised.

In embodiments of the system 100, one or more functions of the external communication device 110 and/or programmer 112 may be integrated into the IMD 102, the EMD 106, the user device 116, and/or the mobile device 118. In some embodiments, the devices may communicate directly with the management server 114, which may be located in the subject's home and/or at a remote location (e.g., the server 114 may be implemented, at least in part, as software having components instantiated by more than one device). The devices 102, 106, 110, and/or 112 may incorporate multimode wireless telecommunications such as cellular, BLUETOOTH, or IEEE 802.11B to communicate with the networks 120 and/or 122.

In embodiments, various devices of the system 100 may be configured to communicate during a given duty cycle. For example, the IMD 102, EMD 106, external communication device 110 and/or programmer 112 may be configured to communicate with the management server 114 (or other device) at given intervals, such as once a week. The IMD 102, EMD 106, external communication device 110 and/or programmer 112 may record data for the time period (e.g., a week) and transmit the data to the management server 114 (or other device) during the portion of the cycle that transmission is active and then conserve energy for the rest of the cycle. In another example, the IMD 102, EMD 106, external communication device 110 and/or programmer 112 conserve energy and only communicates with the management server 114 (or other device) when a trigger event or execution of a study prescription has occurred.

Various components depicted in FIG. 1 may operate together to form the monitoring system 100, which may be, for example, a computerized patient management and monitoring system. In embodiments, the system 100 may be designed to assist in monitoring the subject's condition, managing the subject's therapy, and/or the like. An illustrative patient management and monitoring system is the LATITUDE® patient management system from Boston Scientific Corporation, Natick Mass. Illustrative aspects of a patient management and monitoring system are described in ADVANCED PATIENT MANAGEMENT SYSTEM INCLUDING INTERROGATOR/TRANSCEIVER UNIT, U.S. Pat. No. 6,978,182 to Mazar et al., the entirety of which is hereby incorporated by reference herein.

Patient management and monitoring systems can provide large amounts of data about patients to users such as, for example, clinicians, patients, researchers, and/or the like. For example, such systems can store information about patient characteristics, patient sensor readings including electrocardiograms (EGMs), device settings, therapy deliveries, and/or the like. For example, in embodiments, medical devices such as the IMD 102 and/or the EMD 106 may obtain parameter values that include information associated with an arrhythmia episode or other episode experienced by the patient. As it is used herein, the term "episode" refers to a time period during which some sort of abnormal event occurs. For example, an episode may refer to an arrhythmia, a sleep disturbance (e.g., an apnea episode, a snoring episode, etc.), a psychological episode (e.g., a seizure or other epileptic episode), and/or the like. "Episode data" may include physiological parameter values obtained before, during and/or after an episode, and may also include device settings, actions that were taken by the device, actions that were taken by a user, environmental parameters, and/or other information.

The episode data, or part of the episode data, corresponding to a particular episode may be analyzed using one or more adjudication algorithms to determine one or more classifications of the episode. For example, arrhythmia adjudication algorithms may be used to determine arrhythmia classifications and/or other types of characterizations about an arrhythmia episode; a sleep disturbance adjudication algorithm may be used to determine sleep disturbance classifications and/or other types of characterizations about a sleep disturbance episode; a psychological abnormality adjudication algorithm may be used to determine psychological abnormality classifications and/or other types of characterizations about a psychological episode; and/or the like.

According to embodiments, an adjudication algorithm may be used to detect a particular event, referred to herein as a "trigger event," that prompts further data gathering and analysis (e.g., further adjudications). For example, a medical device (e.g., the IMD 102 and/or the EMD 106) may obtain a first set of information, which may be analyzed to detect a trigger event. The trigger event may be, for example, a certain heart rate, EGM feature, snoring episode, apnea episode, and/or the like. In response to detecting the trigger event, the system may generate a study prescription that, when executed, facilitates enabling the IMD 102 to perform at least a portion of a study. As the term is used herein, a "study" is a monitoring activity that involves obtaining certain parameter values, storing certain parameter values, transmitting certain parameter values, and/or analyzing certain parameter values according to a study prescription, which includes one or more instructions, rules, schemes, and/or the like. For example, in embodiments, a study prescription may include a communication scheme that is configured based on IMD power consumption associated with information transmission from the IMD 102 to an EMD 106 or other device. In executing a study prescription, one or more components of the system 100 obtain and/or store a second set of information that may be analyzed using one or more adjudication algorithms to classify an episode, characterize the condition of a component of the IMD (e.g., a lead integrity), audit the effectiveness of a therapy regimen, and/or the like.

According to embodiments, classifications and/or characterization data can be stored in an adjudication database. In some examples, the characterization data may be sent to the medical device (e.g., IMD 102 and/or EMD 106) to be stored. Once a classification (e.g., an arrhythmia classification) has been generated for a particular episode or a group of episodes, it may be possible to provide patients and/or clinicians with many different types of reports related to the episode data. It may also be possible for the system to analyze the classifications and/or characterization data to provide programming recommendations for a medical device where certain conditions are present. It may also be possible to query the adjudication database for many different types of information that may be useful to clinicians, researchers, regulators, and/or the like.

In embodiments, episode adjudication for detecting a trigger event may be done by the IMD 102 and/or by the EMD 106. For example, a controller or controllers may be configured to extract certain features from a set of information that may include episode data, which may be useful in classifying an episode. The features may, in embodiments, be based on domain knowledge used by clinicians, engineers, technicians, and/or the like to classify the episode data. For example, in embodiments, an electrogram may be used to determine if an arrhythmia episode originates from the atrium or ventricle of the heart through analyzing the timing of the atrial and ventricle activities. The determination can alternatively or additionally be based on the morphology information from the electrograms from different atrial and ventricular channels. In embodiments, episode adjudication for detecting a trigger event may be performed by any number of different components, and/or combinations of components, of the system 100.

According to embodiments, the management server 114 may be used to analyze information obtained in accordance with a study prescription. In embodiments, the management server 114 may additionally, or alternatively, be configured to detect a trigger event, generate a study prescription, provide reports to user devices 116 and/or mobile devices 118, manage patient information, configure therapy regimens, manage/update device software, and/or the like. In embodiments, the management server 114 may be, include, or be included within a server, a server cluster, a computer system, a cloud platform, an enterprise network, and/or the like. Additionally, although illustrated as a device, the management server 114 may, in embodiments, be implemented, at least in part, as software instantiated by any number of devices.

The management server 114 may, for example, index information using a database 124. The database 124 may be, or include, one or more tables, one or more relational databases, one or more multi-dimensional data cubes, one or more non-relational databases, and/or the like. Further, though illustrated as a single component, the database 124 may, in fact, be a plurality of databases 124 such as, for instance, a database cluster, which may be implemented on a single computing device or distributed among a number of computing devices, memory components, or the like.

The management server 114 may be configured to perform security functions, verification functions, and/or the like. Due to potential risks associated with inaccurate adjudication of episodes, detection of triggers, and adjustments in therapy provided by medical devices, it may be desirable for aspects of an at least partially automated system 100 to include safeguards such as, for example, verification of calculations, clinician oversight, and/or the like.

For example, before a study prescription is provided to the IMD 102, the management server 114 may provide a notification of the study prescription to a clinician or other user via the user device 116, mobile device 118, and/or the like. The user (e.g., clinician), in response to receiving the notification, may request a description of the study prescription. In embodiments, the notification of the study prescription may include a description thereof, and may include an indication of a longevity impact associated with the study prescription. As is explained in further detail below, a value may be determined that reflects an impact on the longevity of one or more components of the IMD 102 that is likely to result from execution of a particular study prescription. By presenting this longevity impact value to a user, along with a description of the study prescription, the user is provided with an opportunity to allow the study prescription to be executed or to prevent execution thereof, depending on whether the user believes that the impact on the longevity of the device is outweighed by the potential benefits of executing the study prescription. According to embodiments, the system 100 may include a component that performs this analysis in an automated fashion, based on criteria that may be provided by users and/or learned using a machine-learning technique.

The user (or component or automated process) may provide a confirmation (or denial) of the study prescription to the management server 114. In response to receiving the confirmation, the management server 114 may proceed with providing the study prescription to the IMD 102 for execution. In this manner, embodiments facilitate obtaining a confirmation of a study prescription, or aspects thereof, before implementing the study prescription. In embodiments, for example, a study prescription may be provided to the IMD 102 but may not be executable by the IMD 102 until the IMD 102 receives an enablement command from another device such as, for example, the EMD 106, the external communications device 110, the management server 114, and/or the like. The enablement command may be provided upon receiving a confirmation of the study prescription by, for example, a clinician. According to embodiments, the management server 114 may be configured to provide any number of other, or alternative, functions associated with patient management and/or monitoring.

In embodiments, the system 100 may be configured so that various components of the system 100 provide reporting to various individuals (e.g., patients and/or clinicians). For example, different levels of reporting may be provided by (1) the EMD 106 and/or the external communications device 110 and (2) the management server 114. The EMD 106 and/or the external communications device 110 may be configured to conduct preliminary analysis of data gathered from the IMD 102, and provide reporting should an acute situation (e.g., an episode such as a trigger event) be detected. For example, if the EMD 106 and/or the external communications device 110 detects that a significant heart arrhythmia is imminent or currently taking place, the EMD 106 and/or the external communications device 110 may provide reporting to the patient in the form of an audible or visual alarm.

In addition to forms of reporting including visual and/or audible information, the system 100 may also communicate with and/or reconfigure one or more of the devices 102, 106, 110, and/or 112. For example, if the IMD 102 is part of a cardiac rhythm management system, the management server 114 may communicate with the device 102 and reconfigure the therapy provided by the cardiac rhythm management system based on the data collected from one or more of the devices 102, 106, 110, and/or 112. In another embodiment, the management server 114 may provide to the EMD 106 and/or the external communications device 110 recorded data, an ideal range for the data, a conclusion based on the recorded data, and/or a recommended course of action. This information may be displayed on the EMD 106 and/or the external communications device 110 for the patient to review or made available for the patient and/or clinician to review.

Any number of various components of the system 100 depicted in FIG. 1 may be communicatively coupled via the networks 120 and/or 122. FIG. 1 illustrates one embodiment for the communication system 100. The networks 120 and/or 122 may be, or include, any number of different types of communication networks such as, for example, a bus network, a short messaging service (SMS), a local area network (LAN), a wireless LAN (WLAN), a wide area network (WAN), the Internet, a P2P network, custom-designed communication or messaging protocols, and/or the like. The networks 120 and/or 122 may include a combination of multiple networks.

A variety of communication methods and protocols may be used to facilitate communication between devices 102, 106, 110, 112, 114, 116, and/or 118. For example, wired and wireless communications methods may be used. Wired communication methods may include, for example and without limitation, traditional copper-line communications such as DSL, broadband technologies such as ISDN and cable modems, and fiber optics, while wireless communications may include cellular, satellite, radio frequency (RF), Infrared, etc.

For any given communication method, a multitude of standard and/or proprietary communication protocols may be used. For example and without limitation, protocols such as radio frequency pulse coding, spread spectrum, direct sequence, time-hopping, frequency hopping, SMTP, FTP, and TCP/IP may be used. Other proprietary methods and protocols may also be used. Further, a combination of two or more of the communication methods and protocols may also be used.

The various communications between the components of the system 100 may be made secure using several different techniques. For example, encryption and/or tunneling techniques may be used to protect data transmissions. Alternatively, a priority data exchange format and interface that are kept confidential may also be used. Authentication may be implemented using, for example, digital signatures based on a known key structure (e.g., PGP or RSA). Other physical security and authentication measures may also be used, such as security cards and biometric security apparatuses (e.g., retina scans, iris scans, fingerprint scans, veinprint scans, voice, facial geometry recognition, etc.). Conventional security methods such as firewalls may be used to protect information residing on one or more of the storage media of the advanced patient management system 100. Encryption, authentication and verification techniques may also be used to detect and correct data transmission errors.

In embodiments, varying levels of security may be applied to communications depending on the type of information being transmitted. For example, in embodiments, the management server 114 (or other device) may be configured to apply stricter security measures to confidential health care information than to demographic information. Similarly, even more security may be applied to communications of information used for controlling therapy, adjudicating episodes, and/or the like.

Additionally, in embodiments, communications among the various components of the system 100 may be enhanced using compression techniques to allow large amounts of data to be transmitted efficiently. For example, the devices 102, 106, 110, 112, 114, 116, and 118 may compress information prior to transmitting the information to another device. In embodiments, adaptive compression techniques may be employed such as, for example, the techniques disclosed in U.S. Pat. No. 8,849,682, the entirety of which is hereby incorporated by reference herein.

The illustrative patient management and monitoring system 100 shown in FIG. 1 is not intended to suggest any limitation as to the scope of use or functionality of embodiments of the present disclosure. Neither should the illustrative system 100 be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

Figure 2:
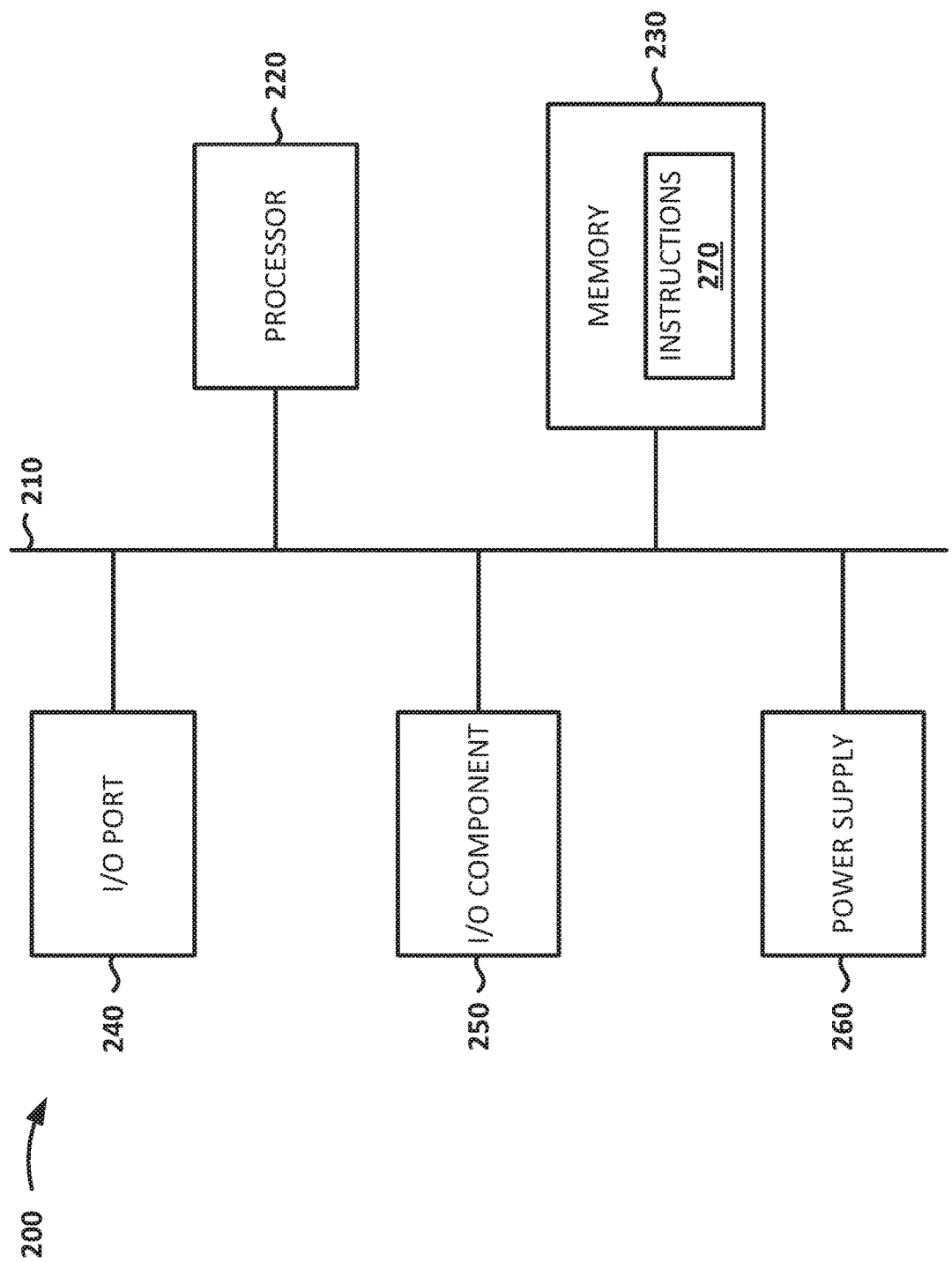
FIG. 2 shows a block diagram depicting an illustrative computing device, in accordance with embodiments of the present disclosure.

According to various embodiments of the disclosed subject matter, any number of the components depicted in FIG. 1 (e.g., the IMD 102, the EMD 106, the external communication device 110, the programmer 112, the management server 114, the mobile device 116, and/or the user device 118) may be implemented on one or more computing devices. FIG. 2 is a block diagram depicting an illustrative computing device 200, in accordance with embodiments of the disclosure. The computing device 200 may include any type of computing device suitable for implementing aspects of embodiments of the disclosed subject matter. Examples of computing devices include specialized computing devices or general-purpose computing devices such "workstations," "servers," "laptops," "desktops," "tablet computers," "handheld devices," "general-purpose graphics processing units (GPGPUs)," and the like, all of which are contemplated within the scope of FIGS. 1 and 2, with reference to various components of the system 100 and/or computing device 200.

In embodiments, the computing device 200 includes a bus 210 that, directly and/or indirectly, couples the following devices: a processor 220, a memory 230, an input/output (I/O) port 240, an I/O component 250, and a power supply 260. Any number of additional components, different components, and/or combinations of components may also be included in the computing device 200. The I/O component 250 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus 210 represents what may be one or more busses (such as, for example, an address bus, data bus, or combination thereof). Similarly, in embodiments, the computing device 200 may include a number of processors 220, a number of memory components 230, a number of I/O ports 240, a number of I/O components 250, and/or a number of power supplies 260. Additionally any number of these components, or combinations thereof, may be distributed and/or duplicated across a number of computing devices.

In embodiments, the memory 230 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 230 stores computer-executable instructions 270 for causing the processor 220 to implement aspects of embodiments of system components discussed herein and/or to perform aspects of embodiments of methods and procedures discussed herein.

The computer-executable instructions 270 may include, for example, computer code, machine-useable instructions, and the like such as, for example, program components capable of being executed by one or more processors 220 associated with the computing device 200. Program components may be programmed using any number of different programming environments, including various languages, development kits, frameworks, and/or the like. Some or all of the functionality contemplated herein may also, or alternatively, be implemented in hardware and/or firmware.

The illustrative computing device 200 shown in FIG. 2 is not intended to suggest any limitation as to the scope of use or functionality of embodiments of the present disclosure. Neither should the illustrative computing device 200 be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 3:
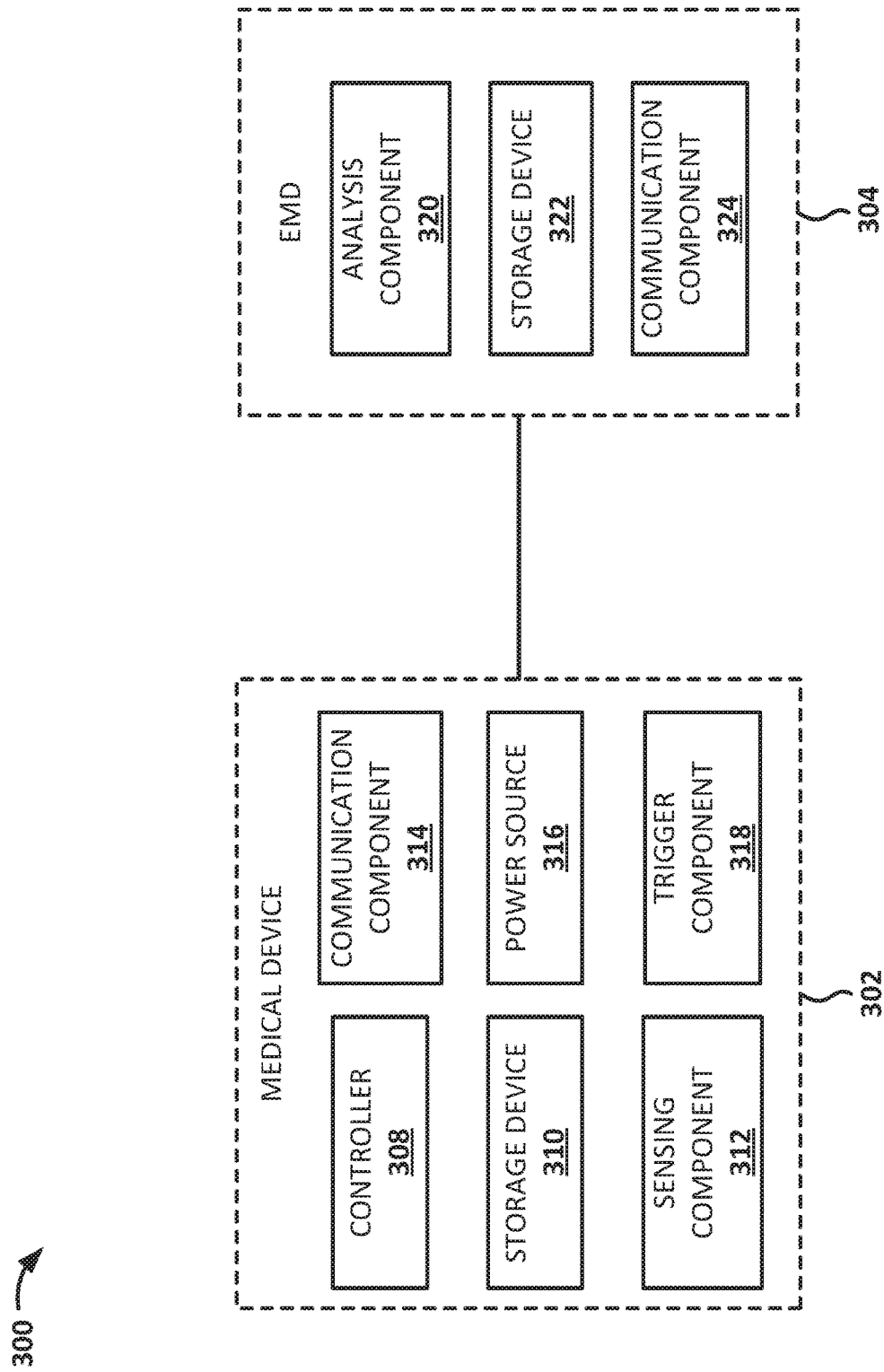
FIG. 3 shows a block diagram depicting an illustrative patient monitoring system, in accordance with embodiments of the present disclosure.

FIG. 3 is a block diagram depicting an illustrative patient monitoring system 300, in accordance with embodiments of the disclosure. As shown, the system 300 includes a medical device 302 (e.g., an IMD or an external medical device) and an EMD 304. Embodiments of the system may include more than one medical devices 302 and/or more than one EMDs 304. The medical device 302 may be, be similar, to, include, or be included in, the IMD 102 depicted in FIG. 1 and/or the EMD 106 depicted in FIG. 1; and the EMD 304 may be, be similar to, include, or be included in, the EMD 106, programmer 112, the user device 116, the mobile device 118, the user and/or the external communication device 110 depicted in FIG. 1. The EMD 304 may be, be similar to, include, or be included within the computing device 200 depicted in FIG. 2.

According to embodiments illustrated in FIG. 3, the medical device 302 includes a controller 308, a storage device 310, a sensing component 312, a communication component 314, a power source 316, and a trigger component 318. The controller 308 may include, for example, a processing unit, a pulse generator, and/or the like. The controller 308 may be any arrangement of electronic circuits, electronic components, processors, program components and/or the like configured to store and/or execute programming instructions, to direct the operation of the other functional components of the medical device 102, to perform arrhythmia detection and/or classification algorithms, to store physiologic data obtained by the sensing component 312, and/or the like, and may be implemented, for example, in the form of any combination of hardware, software, and/or firmware.

In embodiments, the controller 308 may be a programmable micro-controller or microprocessor, and may include one or more programmable logic devices (PLDs) or application specific integrated circuits (ASICs). In some implementations, the controller 308 may include memory as well. Although embodiments of the present system 300 are described in conjunction with a medical device 302 having a microprocessor-based architecture, it will be understood that the medical device 302 (or other device) may be implemented in any logic-based integrated circuit architecture, if desired. The controller 308 may include digital-to-analog (D/A) converters, analog-to-digital (A/D) converters, timers, counters, filters, switches, and/or the like. The controller 308 may execute instructions and perform desired tasks as specified by the instructions.

The controller 308 may also be configured to store information in the storage device 310 and/or access information from the storage device 310. The storage device 310 may be, be similar to, include, or be included within, the storage device 230 depicted in FIG. 2. That is, for example, the storage device 310 may include volatile and/or non-volatile memory, and may store instructions that, when executed by the controller 308 cause methods and processes to be performed by the medical device 302. In embodiments, the controller 308 may process instructions and/or data stored in the storage device 312 to control delivery of an electrical stimulation therapy by the medical device 302, to control sensing operations performed by the medical device 302, to control communications performed by the medical device 302, and/or the like.

The medical device 302 may sense physiological parameter signals using a sensing component 312 that may include, for example, one or more electrodes (not shown), one or more sensors (not shown), or a combination of these. In embodiments, the sensing component 312 may include any number of electrical circuits, electronic components, processors, program components and/or the like. The storage device 310 may be used to store sensed information according to some implementations. Information from sense circuits included in the sensing component 312 may be used to adjust therapy, sensing, and/or communications parameters.

In embodiments, the sensing component 312 may be configured to sense intrinsic cardiac electrical signals in a manner similar to known electrocardiogram (ECG) electrodes, which signals are transmitted via conventional techniques to the controller 308. In various embodiments, the sensing component 312 may be configured to sense other patient physiologic or environmental parameters in addition to, or alternative to, cardiac signals. In embodiments, the sensing component 312 may include temperature sensors (e.g., thermocouples or thermistors), barometers, acoustic sensors, pressure sensors, optical sensors, motion or impact sensors (e.g., accelerometers, inertial measuring units (IMUs)), strain sensors, Doppler systems, ultrasound sensors, and/or the like, in any number of various types of configurations. The foregoing sensors allow the IMD 302 to be capable of sensing and recording physiologic parameters such as, for example, patient movement, posture, respiratory cycles, heart sounds, and/or the like. The output from the sensing component 312 may be used in arrhythmia detection and classification, therapy selection, trigger event detection, study prescription performance, and/or the like.

The communication component 314 may include, for example, circuits, program components, and one or more transmitters and/or receivers for communicating wirelessly with one or more other devices such as, for example, the EMD 304. According to various embodiments, the communication component 314 may include one or more transmitters, receivers, transceivers, transducers, and/or the like, and may be configured to facilitate any number of different types of wireless communication such as, for example, radio-frequency (RF) communication, microwave communication, infrared communication, acoustic communication, inductive communication, conductive communication, and/or the like. The communication component 314 may include any combination of hardware, software, and/or firmware configured to facilitate establishing, maintaining, and using any number of communication links. In embodiments, the communication component 314 of the medical device 302 facilitates wireless communication with the EMD 304. In embodiments, the communication component 314 may also facilitate communications with other medical devices such as, for example, to facilitate coordinated operations between the medical devices.

In other embodiments, other forms of wireless telemetry may be utilized for communications. For example, in embodiments, other RF telemetry technologies may be employed. Alternatively, and/or additionally, inductive telemetry, acoustic telemetry and/or the like may be employed for communicating with, e.g., the EMD 304. In embodiments, conductive telemetry may be employed, in which case, for example, the communication component 314 may interact with one or more sensing/therapy electrode(s) to transmit and/or receive communications encoded in electrical pulses.

The power source 316 provides electrical power to the other operative components (e.g., the controller 308, the sensing component 310, the storage device 312, and the communication component 314), and may be any type of power source suitable for providing the desired performance and/or longevity requirements of the medical device 102. In various embodiments, the power source 316 may include one or more batteries, which may be rechargeable (e.g., using an external energy source). The power source 316 may include one or more capacitors, energy conversion mechanisms, and/or the like. Power sources for medical devices such as the medical device 102 are well known, and are therefore not discussed in greater detail herein.

As shown in FIG. 3, the medical device 302 includes a trigger component 318. In embodiments, the trigger component 318 may be implemented in any combination of hardware, software, and/or firmware, and may be implemented, at least in part, by the controller 308 of the medical device 302. The trigger component 318 is configured to detect a trigger event. According to embodiments, the trigger component 318 may be configured to implement any number of different adjudication algorithms to detect a trigger event. The trigger component 318 may detect a trigger event based on information received from any number of other components, devices, and/or the like. For example, the trigger component 318 may obtain physiological parameter signals from the sensing component 312 and may use that physiological parameter signals to detect a trigger event. Trigger events may be user defined, system defined, statically defined, dynamically defined, and/or the like. The trigger component 318 may reference trigger criteria stored in memory (e.g., the storage device 322) to determine whether a trigger event has occurred. The trigger criteria may be established by a clinician, a patient, an algorithm, and/or the like.

For example, in embodiments, the trigger component 318 may reference a first set of trigger criteria for determining whether a first trigger event has occurred, a second set of trigger criteria for determining whether a second trigger event has occurred, and/or the like. The first trigger event may be, for example, a potential arrhythmia episode (e.g., a potential atrial fibrillation episode), detected based on an R-R variability exceeding a variability threshold. Any number of techniques for analyzing R-R variability can be used such as those described in U.S. application Ser. No. 14/825,669, titled "ATRIAL FIBRILLATION DETECTION USING VENTRICULAR RATE VARIABILITY," the disclosure of which is hereby incorporated by reference herein in its entirety. Because different patients may have different cardiac characteristics, the trigger criteria for detecting a potential arrhythmia as a trigger event may be different for a first patient than it is for a second patient. In some embodiments, the first trigger event is initiated upon detecting a change in heart rate that exceeds a threshold. As mentioned above, the trigger component 318 and associated trigger criteria may be set to be sensitive and therefore over inclusive to mitigate missing a potential AF episode. If it is determined that trigger criteria is too sensitive (e.g., many false positives), sensitivity of the trigger component can be decreased by raising a threshold for initiating a first trigger event.

Additionally, in the context of a single patient, a variability threshold may be different depending on the situation. For example, to detect a trigger event based on an R-R variability, the trigger component 318 may also be configured to obtain information from a position sensor (e.g., an accelerometer), a motion sensor, a respiration sensor (e.g., a minute volume component implemented in the medical device 302), and/or the like. A set of trigger criteria also may be dynamically adapted over time, using a machine-learning process. That is, for example, as a patient ages, adopts changes to daily routines (e.g., diet, exercise, sleep habits), and/or the like, the trigger component 318 may dynamically adapt trigger criteria so that, for example, a different R-R variability may be detected as a trigger event when the patient is older than when the patient was younger. Additionally, machine-learning techniques may be employed to adapt trigger criteria to more rapidly-changing scenarios such as, for example, the impact of adjusting to a new medication, the impact of a temporary adjustment in sleep schedule, the impact of the air quality in a particular location (e.g., outside vs. inside, downtown vs. at home, one city vs. another), the impact of an allergic reaction to an environmental stimulus, the impact of a psychological response to an increase or decrease in an amount of sunlight over the course of one or more days, the impact of a rapid change in barometric pressure, and/or the like. According to embodiments, adapting a set of trigger criteria may include adjusting one or more thresholds, adjusting one or more value ranges, adding or subtracting types of information to be considered (e.g., requiring additional, or fewer, inputs to an adjudication algorithm), adjusting weight applied to one or more inputs, adjusting error terms, adjusting boundary conditions, and/or the like.

A trigger event may initiate application of one or more study prescriptions. For example, upon detecting a trigger event, the trigger component 318 may be configured to cause the communication component 314 to transmit information to the EMD 304. In other embodiments, the trigger component 318 is configured to automatically cause the communication component 314 to transmit information to the EMD 304. The information may include a variety of physiological parameters sensed by the IMD 302. In addition, a trigger event may cause sensors external to the IMD to communicate information to the EMD 304 for correlation and analysis by the EMD. In embodiments, all episode information is communicated. In other embodiments, only selected regions of interest are communicated—as prescribed by a given study prescription. For example, the IMD 302's communication component 314 may only send information (e.g., heart sounds, activity) related to beats that are close to thresholds. Limiting an amount of information communicated may reduce power consumption and therefore extend battery life, for example.

As shown in FIG. 3, the EMD 304 includes an analysis component 320, a storage device 322, and a communication component 324. In embodiments, the analysis component 320 may be implemented in any combination of hardware, software, and/or firmware, and may be implemented, at least in part, by a controller (not shown) that may be identical to, or similar to, the controller 308 of the IMD 302. Additionally, the storage device 322 and communication component 324 may be identical to, or similar to, the storage device 310 and the communication component 314, respectively, of the IMD 302. The EMD 304 may include any number of other components or combination of components including, for example, a sensing component, a therapy component, and/or the like.

In embodiments, the analysis component 320 may perform or apply a more accurate (and therefore likely more computationally expensive) analysis than the trigger component 318 upon receiving information communicated to the EMD 304 from the IMD 302. Upon analyzing the information, the analysis component 320 can confirm whether an AF episode occurred. In embodiments, the analysis component 320 analyzes the information based on a heart rate density index, which is described in U.S. Pat. No. 8,929,981 and is hereby incorporated by reference in its entirety. In embodiments, the analysis component 320 analyzes the information for R-events detected based on morphology analysis and template matching, which is described in U.S. Pat. No. 6,490,479 and is hereby incorporated by reference in its entirety. In embodiments, the analysis component 320 analyzes the information by identifying and discarding premature ventricular contractions or inaccurate R-wave detections through morphology analysis and template matching, which is described in U.S. Pat. No. 7,751,876 and is hereby incorporated by reference in its entirety, and re-running R-R variability analysis on the remaining beats. In some embodiments, the beats immediately preceding and succeeding the discarded beats are also discarded. In embodiments, the analysis component 320 analyzes the information including heart sound data to determine whether an AF episode occurred. For example, the analysis component 320 may analyze heart sound data for 51 amplitude variability, S1 amplitude versus heart rate dissociation, relationships of systolic time intervals with heart rate, presence of S4 heart sound, and/or combination of presence of P-wave and S4. Various heart sound analyses are described in U.S. Pat. Pub. Nos. 2013/0237773, 2014/0277243, and 2015/0342487— each of which are incorporated by reference in their entirety. In some embodiments, the analysis of heart sound data is limited to beats that are not discarded based on morphology analysis and template matching.

According to embodiments, the analysis component may be configured to identify and discard pairs of beats that are within a specified neighborhood of a threshold and in which either a P-wave or an S4 heart sound is detected, and re-runs the same algorithm as implemented by the trigger component (such as the R-R variability analysis) on the remaining beats. In embodiments, the physiological signal associated with the detection of the episode may be divided into sections, and a confirmation analysis run on each of the sections.

The storage device 322 may be similar to the storage device 310. That is, for example, the storage device 322 may include volatile and/or non-volatile memory, and may store instructions that, when executed by a controller cause methods and processes to be performed by the EMD 302. In embodiments, the controller may process instructions and/or data stored in the storage device 322 to control communications performed by the communication component 324.

The communication component 324 may communicate with a variety of devices described in detail above. For example, if the EMD's analysis component 320 confirms that an AF episode has occurred, the communication component 324 may initiate an alarm signal to the patient or physician or generate a report for visual display for additional review and analysis.

The illustrative patient monitoring system 300 shown in FIG. 3 is not intended to suggest any limitation as to the scope of use or functionality of embodiments of the present disclosure. Neither should the illustrative patient monitoring system 300 be interpreted as having any dependency or requirement related to any single component or combination of components illustrated therein. Additionally, various components depicted in FIG. 3 may be, in embodiments, integrated with various ones of the other components depicted therein (and/or components not illustrated), all of which are considered to be within the ambit of the present disclosure.

Figure 4:
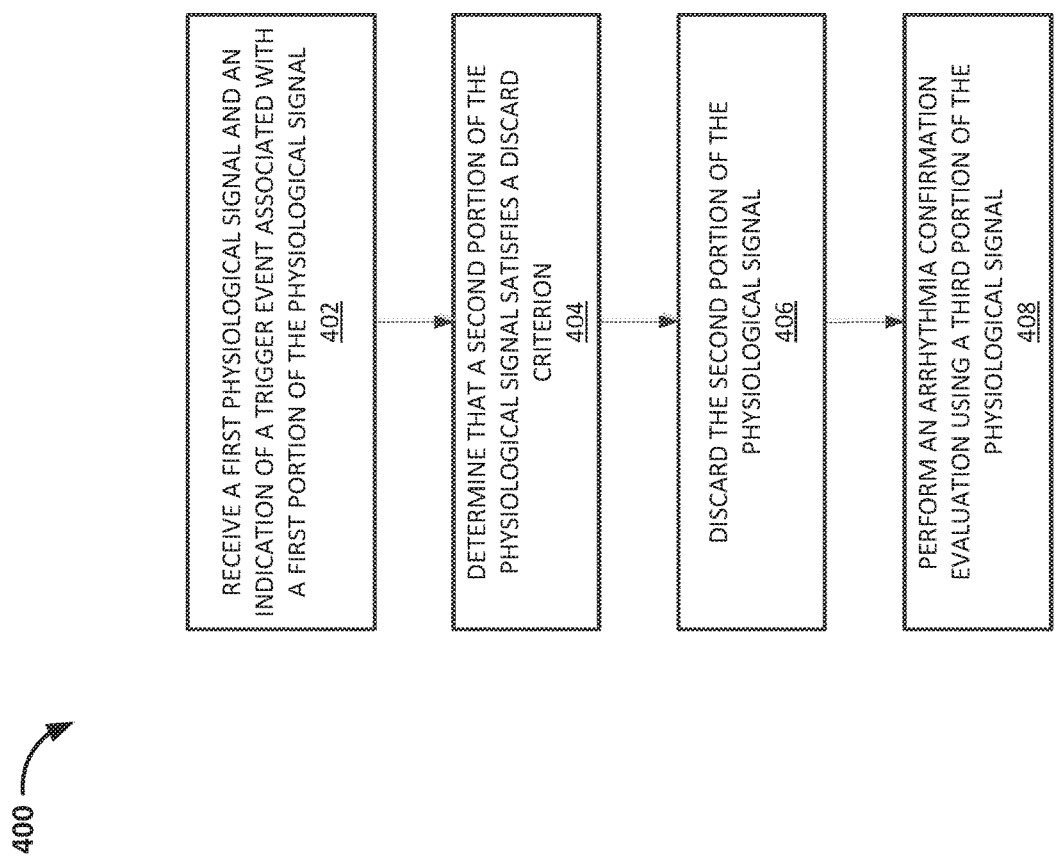
FIG. 4 shows a flow diagram depicting an illustrative method of monitoring a subject for an arrhythmia, in accordance with embodiments of the present disclosure.

FIG. 4 is a flow diagram depicting an illustrative method 400 of monitoring a subject for an arrhythmia, in accordance with embodiments of the disclosure. Embodiments of the method 400 may be performed by a medical device and/or other device (e.g., the IMD 102 depicted in FIG. 1, the EMD depicted in FIG. 1, the external communication device 110 depicted in FIG. 1, the programmer 112 depicted in FIG. 1, the server 114 depicted in FIG. 1, the user device 116 depicted in FIG. 1, the mobile device 118 depicted in FIG. 1, the medical device 302 depicted in FIG. 3, the EMD 304 depicted in FIG. 3). Embodiments of the method 400 include receiving, from a medical device, a first physiological parameter signal and an indication of a detected trigger event associated with a first portion of the first physiological parameter signal (block 402). In embodiments, the trigger event is indicative of a potential arrhythmia.

Embodiments of the method 400 further include determining that a second portion of the first physiological parameter signal satisfies a discard criterion (block 404); discarding the second portion (block 406); and performing an arrhythmia confirmation evaluation using a third portion of the first physiological parameter signal (block 408). In embodiments, determining that a second portion of the first physiological parameter signal satisfies a discard criterion includes identifying a set of beat pairs within a specified neighborhood of a variability threshold; and detecting at least one of a P-wave and an S4 heart sound corresponding to each of a subset of the set of beat pairs, where the subset of beat pairs includes the second portion of the first physiological parameter signal. To that end, embodiments of the method 400 may include receiving a second physiological signal, the second physiological signal including a heart sounds signal.

According to embodiments, the trigger event may be detected based on a first R-R variability associated with a first portion of the physiological signal exceeding a variability threshold, and performing the arrhythmia confirmation algorithm may include calculating a second R-R variability associated with the third portion of the first physiological parameter signal; and determining that the second R-R variability exceeds the variability threshold. Embodiments of the method 400 may be further iterated in a manner such that the method 400 further includes dividing the first portion of the first physiological signal into a number of sections; determining that a first portion of each section satisfies the discard criterion; discarding the first portion of each section; and performing an arrhythmia confirmation evaluation using a second portion of each section.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A system, comprising:
a medical device operatively coupled to a subject's body, the medical device comprising:
a sensing component configured to obtain a first physiological parameter signal;
a trigger component configured to detect, based on a first portion of the first physiological parameter signal, a trigger event indicative of a potential arrhythmia, wherein to detect the trigger comprises: calculating a first R-R variability associated with the first portion of the first physiological parameter signal; and determining that the first R-R variability exceeds a variability threshold;
a first communication component configured to transmit the first physiological parameter signal; and an external monitoring device (EMD) configured to be disposed outside of the subject's body, the EMD comprising:
  a second communication component configured to receive, from the first communication component, the first physiological parameter signal; and
  an analysis component configured to (1) identify a second portion of the first physiological parameter signal, wherein the second portion satisfies a discard criterion that is determined using template matching, morphology analysis, or both, (2) discard the second portion, and (3) perform an arrhythmia confirmation evaluation using a third portion of the first physiological parameter signal.

2. The system of claim 1, wherein the trigger event comprises a potential atrial fibrillation episode.

3. The system of claim 1, wherein the trigger component is configured to cause, in response to detecting the trigger event, the first communication component to transmit the first physiological parameter signal to the second communication component.

4. The system of claim 1, wherein the analysis component is configured to identify the second portion of the first physiological parameter signal by:
  identifying a set of beat pairs within a specified neighborhood of the variability threshold; and
  detecting at least one of a P-wave and an S4 heart sound corresponding to each of a subset of the set of beat pairs, wherein the subset of beat pairs comprises the second portion of the first physiological parameter signal.

5. The system of claim 4, wherein the sensing component is further configured to obtain a second physiological parameter signal, the second physiological parameter signal comprising a heart sounds signal.

6. The system of claim 4, wherein the analysis component is configured to perform the arrhythmia confirmation algorithm by:
  calculating a second R-R variability associated with the third portion of the first physiological parameter signal; and
  determining that the second R-R variability exceeds the variability threshold.

7. The system of claim 1, wherein the analysis component is further configured to:
  divide the first portion of the first physiological signal into a plurality of sections;
  identify a first portion of each of the plurality of sections, wherein the first portion of each of the plurality of sections satisfies the discard criterion;
  discard the first portion of each of the plurality of sections; and
  perform an arrhythmia confirmation evaluation using a second portion of each of the plurality of sections.

8. The system of claim 1, wherein the medical device comprises an implantable medical device.

9. A method of monitoring a subject for arrhythmia, the method comprising:
  receiving, from a medical device, a first physiological parameter signal and an indication of a detected trigger event associated with a first portion of the first physiological parameter signal, wherein the trigger event is indicative of a potential arrhythmia;
  determining that a second portion of the first physiological parameter signal satisfies a discard criterion that is determined using template matching, morphology analysis, or both and comprises identifying a set of beat pairs within a specified neighborhood of a variability threshold; and detecting at least one of a P-wave and an S4 heart sound corresponding to each of a subset of the set of beat pairs, wherein the subset of beat pairs comprises the second portion of the first physiological parameter signal;
  discarding the second portion; and
  performing an arrhythmia confirmation evaluation using a third portion of the first physiological parameter signal.

10. The method of claim 9, further comprising receiving a second physiological signal, the second physiological signal comprising a heart sounds signal.

11. The method of claim 9, wherein the trigger event is detected based on a first R-R variability associated with a first portion of the physiological signal, and wherein performing the arrhythmia confirmation algorithm comprises:
  calculating a second R-R variability associated with the third portion of the first physiological parameter signal; and
  determining that the second R-R variability exceeds the variability threshold.

12. The method of claim 11, further comprising detecting the trigger event by:
  calculating the first R-R variability associated with the first portion of the first physiological parameter signal; and
  determining that the first R-R variability exceeds the variability threshold.

13. The method of claim 12, wherein performing the arrhythmia confirmation evaluation using the third portion of the first physiological parameter signal comprises:
  detecting a plurality of R waves using a morphology analysis; and
  calculating the second R-R variability based on the plurality of R waves.

14. The method of claim 9, wherein the medical device comprises an implantable medical device.

15. The method of claim 9, further comprising:
  dividing the first portion of the first physiological signal into a plurality of sections;
  determining that a first portion of each of the plurality of sections satisfies the discard criterion;
  discarding the first portion of each of the plurality of sections; and
  performing an arrhythmia confirmation evaluation using a second portion of each of the plurality of sections.

16. A method of monitoring a subject for arrhythmia, the method comprising:
  receiving a first physiological parameter signal and an indication of a detected trigger event associated with a first portion of the first physiological parameter signal, wherein the trigger event is indicative of a potential arrhythmia;
  dividing the first portion of the first physiological parameter signal into a plurality of sections;
  determining that a first portion of each of the plurality of sections satisfies a discard criterion that is determined using template matching, morphology analysis, or both and comprises identifying a set of beat pairs within a specified neighborhood of a variability threshold; and detecting at least one of a P-wave and an S4 heart sound corresponding to each of a subset of the set of beat pairs;
  discarding the first portion of each of the plurality of sections; and
  performing an arrhythmia confirmation evaluation using a second portion of each of the plurality of sections.

17. The method of claim 16, wherein performing the arrhythmia confirmation evaluation using a second portion of the first section comprises:
- calculating an R-R variability associated with the second portion of the first section; and
- determining that the R-R variability exceeds the variability threshold.

\* \* \* \* \*